United States Patent
Newton

(10) Patent No.: US 10,376,406 B2
(45) Date of Patent: Aug. 13, 2019

(54) MALE URINE COLLECTION DEVICE USING WICKING MATERIAL

(71) Applicant: PureWick Corporation, El Cajon, CA (US)

(72) Inventor: Camille Rose Newton, Bonsall, CA (US)

(73) Assignee: PUREWICK CORPORATION, Spring Valley, CA (US)

( * ) Notice: Subject to any disclaimer, the term of this patent is extended or adjusted under 35 U.S.C. 154(b) by 174 days.

(21) Appl. No.: 15/221,106

(22) Filed: Jul. 27, 2016

(65) Prior Publication Data
US 2018/0028348 A1 Feb. 1, 2018

(51) Int. Cl.
*A61F 5/453* (2006.01)
*A61F 5/44* (2006.01)
*A01K 23/00* (2006.01)

(52) U.S. Cl.
CPC ............... *A61F 5/453* (2013.01); *A01K 23/00* (2013.01); *A61F 5/4404* (2013.01)

(58) Field of Classification Search
CPC ...... A61F 5/453; A61F 5/4408; A61F 13/471; A61F 13/4915; A01K 23/00
See application file for complete search history.

(56) References Cited

U.S. PATENT DOCUMENTS

| | | |
|---|---|---|
| 3,349,768 A | 10/1967 | Keane |
| 3,511,241 A * | 5/1970 | Lee .................. A61F 5/453 604/352 |
| 3,651,810 A * | 3/1972 | Ormerod ............ A61F 5/453 604/329 |
| 4,233,025 A | 11/1980 | Larson et al. |

(Continued)

FOREIGN PATENT DOCUMENTS

| | | |
|---|---|---|
| DE | 102011103783 A1 | 12/2012 |
| JP | 2001054531 | 2/2001 |

(Continued)

OTHER PUBLICATIONS

Corrected International Search Report and Written Opinion for International Application No. PCT/US2017/043025 dated Jan. 11, 2018.

(Continued)

*Primary Examiner* — Susan S Su
(74) *Attorney, Agent, or Firm* — Dorsey & Whitney LLP

(57) ABSTRACT

A urine collection device has a chamber assembly, which includes a layer of wicking material and porous material. The porous material is configured to form a chamber in which urine can be collected for transport; and the wicking material is disposed about the porous material. The chamber has a port for receiving a tube so that urine collected within the chamber can be transported from the chamber by being drawn from the chamber when a partial vacuum is applied within the chamber via the received tube. The chamber assembly is so dimensioned and configured that opposing portions of the assembly are sufficiently adjacent as to define an opening through which the head of a penis can be inserted. A layer of impermeable material is so attached to the chamber assembly as to cover one side of the opening and thereby provide a receptacle for receiving the head of an inserted penis.

19 Claims, 1 Drawing Sheet

(56) References Cited

U.S. PATENT DOCUMENTS

| | | | |
|---|---|---|---|
| 4,246,901 A | 1/1981 | Frosch et al. | |
| 4,453,938 A | 6/1984 | Brendling | |
| 4,610,675 A | 9/1986 | Triunfol | |
| 4,627,846 A | 12/1986 | Ternstroem | |
| 4,631,061 A | 12/1986 | Martin | |
| 4,650,477 A | 3/1987 | Johnson | |
| 4,747,166 A | 5/1988 | Kuntz | |
| 4,772,280 A | 9/1988 | Rooyakkers | |
| 4,790,835 A * | 12/1988 | Elias | A61F 5/453 604/349 |
| 4,795,449 A | 1/1989 | Schneider et al. | |
| 4,846,909 A | 7/1989 | Klug et al. | |
| 4,886,508 A | 12/1989 | Washington | |
| 4,905,692 A | 3/1990 | More | |
| 5,002,541 A | 3/1991 | Conkling et al. | |
| 5,031,248 A | 7/1991 | Kemper | |
| 5,084,037 A * | 1/1992 | Barnett | A61F 5/453 604/349 |
| 5,195,997 A * | 3/1993 | Carns | A61F 5/453 600/519 |
| 5,244,458 A | 9/1993 | Takasu | |
| 5,300,052 A * | 4/1994 | Kubo | A61F 5/453 4/144.1 |
| 5,382,244 A | 1/1995 | Telang | |
| 5,636,643 A | 6/1997 | Argenta et al. | |
| 5,678,564 A | 10/1997 | Lawrence et al. | |
| 5,687,429 A | 11/1997 | Rahlff | |
| 5,695,485 A * | 12/1997 | Duperret | A61F 5/453 604/349 |
| 5,752,944 A * | 5/1998 | Dann | A61F 5/453 604/349 |
| 5,827,247 A | 10/1998 | Kay | |
| 5,827,250 A | 10/1998 | Fujioka et al. | |
| 5,827,257 A | 10/1998 | Fujioka et al. | |
| 5,894,608 A | 4/1999 | Birbara | |
| 5,911,222 A | 6/1999 | Lawrence et al. | |
| 6,063,064 A | 5/2000 | Tuckey et al. | |
| 6,105,174 A | 8/2000 | Karlsten et al. | |
| 6,113,582 A * | 9/2000 | Dwork | A61F 5/453 604/349 |
| 6,117,163 A | 9/2000 | Bierman | |
| 6,123,398 A | 9/2000 | Arai et al. | |
| 6,129,718 A | 10/2000 | Wada et al. | |
| 6,177,606 B1 | 1/2001 | Etheredge et al. | |
| 6,209,142 B1 | 4/2001 | Mattsson et al. | |
| 6,248,096 B1 * | 6/2001 | Dwork | A61F 5/453 604/347 |
| 6,336,919 B1 | 1/2002 | Davis et al. | |
| 6,338,729 B1 | 1/2002 | Wada et al. | |
| 6,409,712 B1 | 6/2002 | Dutari et al. | |
| 6,416,500 B1 * | 7/2002 | Wada | A61F 13/4704 604/346 |
| 6,479,726 B1 | 11/2002 | Cole et al. | |
| 6,540,729 B1 | 4/2003 | Wada et al. | |
| 6,547,771 B2 | 4/2003 | Robertson et al. | |
| 6,592,560 B2 | 7/2003 | Snyder et al. | |
| 6,620,142 B1 * | 9/2003 | Fluckiger | A61F 5/4556 604/349 |
| 6,702,793 B1 | 3/2004 | Sweetser et al. | |
| 6,706,027 B2 | 3/2004 | Harvie et al. | |
| 6,740,066 B2 | 5/2004 | Wolff et al. | |
| 6,814,547 B2 | 11/2004 | Childers et al. | |
| 6,849,065 B2 | 2/2005 | Schmidt et al. | |
| 6,912,737 B2 | 7/2005 | Ernest et al. | |
| 6,918,899 B2 | 7/2005 | Harvie | |
| 7,018,366 B2 | 3/2006 | Easter | |
| 7,131,964 B2 | 11/2006 | Harvie | |
| 7,135,012 B2 | 11/2006 | Harvie | |
| 7,141,043 B2 | 11/2006 | Harvie | |
| 7,171,699 B2 | 2/2007 | Ernest et al. | |
| 7,181,781 B1 | 2/2007 | Trabold et al. | |
| 7,192,424 B2 | 3/2007 | Cooper | |
| 7,220,250 B2 * | 5/2007 | Suzuki | A61F 5/451 604/317 |
| 7,335,189 B2 | 2/2008 | Harvie | |
| 7,699,831 B2 | 4/2010 | Bengtson et al. | |
| 7,866,942 B2 | 1/2011 | Harvie | |
| 7,871,385 B2 | 1/2011 | Levinson et al. | |
| 7,875,010 B2 | 1/2011 | Frazier et al. | |
| 7,901,389 B2 | 3/2011 | Mombrinie | |
| 7,927,321 B2 | 4/2011 | Marland | |
| 7,931,634 B2 | 4/2011 | Swiecicki et al. | |
| 7,993,318 B2 | 8/2011 | Olsson et al. | |
| 8,181,651 B2 | 5/2012 | Pinel | |
| 8,211,063 B2 | 7/2012 | Bierman et al. | |
| 8,241,262 B2 | 8/2012 | Mahnensmith | |
| 8,277,426 B2 | 10/2012 | Wilcox et al. | |
| 8,287,508 B1 | 10/2012 | Sanchez | |
| 8,425,482 B2 * | 4/2013 | Khoubnazar | A61F 13/471 604/349 |
| 8,551,075 B2 | 10/2013 | Bengtson | |
| 8,568,376 B2 | 10/2013 | Delattre et al. | |
| 8,585,683 B2 | 11/2013 | Bengtson et al. | |
| 8,715,267 B2 | 5/2014 | Bengtson et al. | |
| 8,864,730 B2 | 10/2014 | Conway et al. | |
| 8,936,585 B2 | 1/2015 | Carson et al. | |
| 9,248,058 B2 | 2/2016 | Conway et al. | |
| 9,480,595 B2 | 11/2016 | Baham et al. | |
| 2002/0026161 A1 | 2/2002 | Grundke | |
| 2003/0195484 A1 | 10/2003 | Harvie | |
| 2004/0127872 A1 | 7/2004 | Petryk et al. | |
| 2004/0236292 A1 | 11/2004 | Tazoe et al. | |
| 2004/0254547 A1 | 12/2004 | Okabe et al. | |
| 2005/0070862 A1 | 3/2005 | Tazoe et al. | |
| 2005/0097662 A1 | 5/2005 | Leimkuhler et al. | |
| 2005/0101924 A1 * | 5/2005 | Elson | A61F 5/453 604/349 |
| 2005/0177070 A1 | 8/2005 | Levinson et al. | |
| 2005/0279359 A1 | 12/2005 | LeBlanc et al. | |
| 2006/0200102 A1 * | 9/2006 | Cooper | A61F 5/44 604/349 |
| 2006/0229576 A1 * | 10/2006 | Conway | A61F 5/453 604/349 |
| 2006/0235359 A1 | 10/2006 | Marland | |
| 2007/0006368 A1 | 1/2007 | Key et al. | |
| 2008/0234642 A1 * | 9/2008 | Patterson | A61F 5/441 604/319 |
| 2008/0287894 A1 | 11/2008 | Van Den Heuvel et al. | |
| 2009/0025717 A1 | 1/2009 | Pinel | |
| 2009/0056003 A1 | 3/2009 | Ivie et al. | |
| 2009/0281510 A1 * | 11/2009 | Fisher | A61F 5/44 604/349 |
| 2010/0185168 A1 | 7/2010 | Graauw et al. | |
| 2010/0263113 A1 * | 10/2010 | Shelton | A61F 5/453 4/144.2 |
| 2011/0034889 A1 | 2/2011 | Smith | |
| 2011/0040271 A1 | 2/2011 | Rogers et al. | |
| 2011/0054426 A1 | 3/2011 | Stewart et al. | |
| 2011/0202024 A1 | 8/2011 | Cozzens | |
| 2012/0103347 A1 | 5/2012 | Wheaton et al. | |
| 2012/0165768 A1 * | 6/2012 | Sekiyama | A61F 5/453 604/353 |
| 2012/0245547 A1 | 9/2012 | Wilcox et al. | |
| 2012/0330256 A1 | 12/2012 | Wilcox et al. | |
| 2013/0053804 A1 * | 2/2013 | Sorensen | A61F 5/453 604/349 |
| 2014/0031774 A1 | 1/2014 | Bengtson | |
| 2014/0196189 A1 * | 7/2014 | Lee | A41D 13/1245 2/69 |
| 2015/0047114 A1 | 2/2015 | Ramirez | |
| 2015/0209194 A1 * | 7/2015 | Heyman | A61F 13/471 604/385.03 |
| 2015/0366699 A1 | 12/2015 | Nelson | |
| 2016/0100976 A1 | 4/2016 | Conway et al. | |
| 2016/0367226 A1 | 12/2016 | Newton et al. | |
| 2016/0367411 A1 | 12/2016 | Justiz et al. | |
| 2016/0374848 A1 | 12/2016 | Sanchez et al. | |
| 2017/0143534 A1 | 5/2017 | Sanchez | |
| 2017/0189225 A1 | 7/2017 | Voorhees et al. | |

(56) References Cited

U.S. PATENT DOCUMENTS

2017/0042748 A1 12/2017 Griffin
2018/0228642 A1 8/2018 Davis et al.

FOREIGN PATENT DOCUMENTS

WO 9309736 A2 5/1993
WO 2008078117 A1 7/2008

OTHER PUBLICATIONS

International Search Report and Written Opinion for International Application No. PCT/US2017/043025 dated Oct. 18, 2017.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Step by Step How Ur24 WorksHome", http://medicalpatentur24.com, last accessed Dec. 6, 2017, Aug. 30, 2017, 4 pages.
Non-Final Office Action for U.S. Appl. No. 15/238,427 dated Aug. 8, 2018.
Advisory Action for U.S. Appl. No. 14/952,591 dated Jun. 1, 2018.
AMXDmax In-Flight Bladder Relief; Omni Medical 2015; Omni Medical Systems, Inc.
Final Office Action for U.S. Appl. No. 14/952,591 dated Feb. 23, 2018.
Final Office Action for U.S. Appl. No. 14/947,759 dated Apr. 8, 2016.
Final Office Action for U.S. Appl. No. 15/238,427 dated Jan. 2, 2019.
Final Office Action for U.S. Appl. No. 15/260,103 dated Feb. 14, 2019.
International Search Report and Written Opinion for International Application No. PCT/US2018/015968 dated Apr. 6, 2018.
International Search Report and Written Opinion for International Patent Application No. PCT/US16/49274, dated Dec. 1, 2016.
International Search Report and Written Opinion for International Patent Application No. PCT/US2017/035625, dated Aug. 15, 2017.
Non-Final Office Action for U.S. Appl. No. 14/947,759, dated Mar. 17, 2016.
Non-Final Office Action for U.S. Appl. No. 14/952,591 dated Aug. 1, 2017.
Non-Final Office Action for U.S. Appl. No. 14/952,591 dated Sep. 28, 2018.
Non-Final Office Action for U.S. Appl. No. 15/171,968 dated Jun. 12, 2018.
Non-Final Office Action for U.S. Appl. No. 15/260,103 dated Sep. 26, 2018.
Non-Final Office Action for U.S. Appl. No. 15/611,587 dated Jul. 13, 2018.
Non-Final Office Action for U.S. Appl. No. 15/611,587 dated Dec. 29, 2017.
Notice of Allowance for U.S. Appl. No. 15/611,587 dated Dec. 21, 2018.
U.S. Appl. No. 15/171,968, filed Jun. 2, 2016.
U.S. Appl. No. 15/260,103, filed Sep. 8, 2016.
U.S. Appl. No. 15/611,587, filed Jun. 1, 2017.
U.S. Appl. No. 15/612,325, filed Jun. 2, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
Issue Notification for U.S. Appl. No. 15/611,587 dated Feb. 20, 2019.
Parmar, "10 Finalists Chosen for Dare-to-Dream Medtech Design Challenge (PUreWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Final Office Action for U.S. Appl. No. 15/171,968 dated Mar. 19, 2019.
U.S. Appl. No. 15/221,106, filed Jul. 27, 2016.
Advisory Action for U.S. Appl. No. 15/238,427 dated Apr. 10, 2019.
Non-Final Office Action for U.S. Appl. No. 14/952,591 dated Mar. 21, 2019.
Notice of Allowance for U.S. Appl. No. 15/238,427 dated May 23, 2019.
Notice of Allowance for U.S. Appl. No. 15/260,103 dated Jun. 7, 2019.
U.S. Appl. No. 16/369,676 filed Mar. 29, 2019.

* cited by examiner

MALE URINE COLLECTION DEVICE USING WICKING MATERIAL

BACKGROUND OF THE INVENTION

The invention generally pertains to using wicking material to collect urine for transport and is particularly directed to a device that can be used to so collect urine from the penis of a person or an animal in such a manner that the urine can be readily transported from the device as the urine is being collected.

A container for collecting urine and transporting the collected urine voided from a person's body is described in U.S. Pat. No. 8,287,508 to Robert A. Sanchez. The container described in said patent is made of plastic or some other material and defines a chamber for collecting urine. The container is closed, except for having an array of openings through which urine can be drawn into the chamber for collection and at least one port through which urine can be drawn away from the chamber by a transport tube inserted into the chamber. The exterior of the container is configured for enabling a moisture-wicking article to be secured over the array of openings and for enabling the secured moisture-wicking article to be disposed in contact with the region of a female body surrounding the urethral opening. A vacuum pump is attached to the transport tube in order to create a partial vacuum in the chamber in order to draw urine into the chamber for collection of the urine and in order to draw the collected urine away from the chamber.

SUMMARY OF THE INVENTION

The invention provides a device that can be used to so collect urine flowing from the penis of a person or an animal in such a manner that the urine can be readily transported from the device as the urine is being collected, the device comprising: a chamber assembly in which wicking material is disposed about porous material that is configured to form a chamber in which urine can be collected for transport, with the chamber having a port for receiving a tube so that urine collected within the chamber can be transported from the chamber by being drawn from the chamber when a partial vacuum is applied within the chamber via a said received tube, and with the assembly being so dimensioned and configured that opposing portions of the assembly are sufficiently adjacent as to define an opening through which the head of a penis can be inserted; and a layer of impermeable material so attached to the chamber assembly as to cover one side of the opening and thereby provide a receptacle for receiving the head of a said inserted penis, from which receptacle urine flowing from said penis can be drawn through the wicking material and the porous material into the chamber when a said partial vacuum is applied within the chamber via said tube. The chamber includes spaces within the porous material and/or spaces between portions of the configured porous material.

The invention is particularly useful for persons or animals during various circumstances. These circumstances include a condition such as incontinence or a disability that limits or impairs mobility. These circumstances also include restricted travel conditions, such as sometimes experienced by pilots, drivers, workers in hazardous areas, etc. These circumstances further include collection of urine for monitoring purposes or clinical testing.

Additional features of the invention are described with reference to the detailed description.

DETAILED DESCRIPTION

Figure 1:
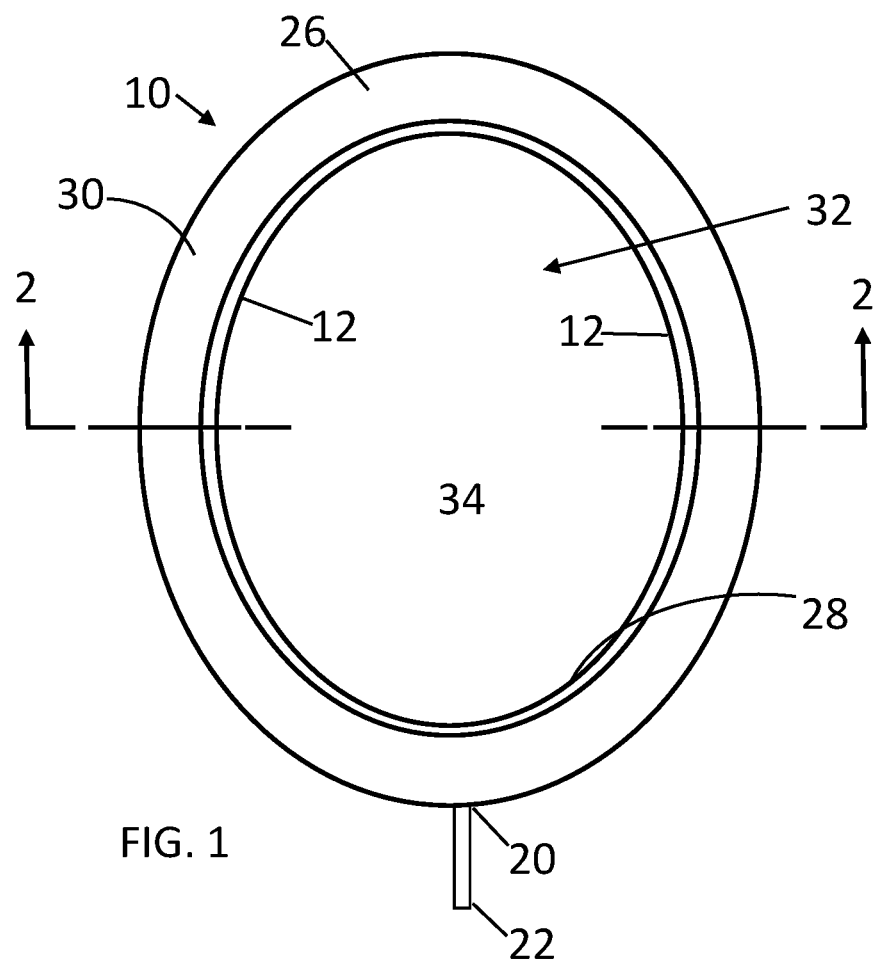
FIG. 1 is a top view of an exemplary embodiment of a urine collection device according to the invention.
Figure 2:
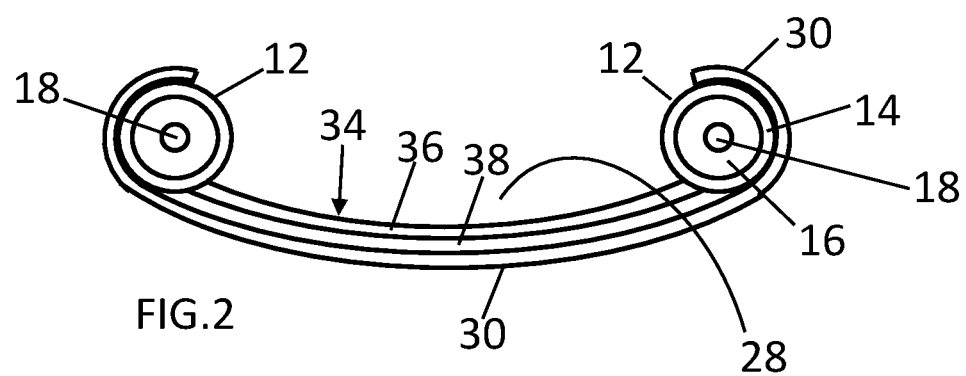
FIG. 2 is a (non-cross-hatched) sectional view taken along line 2-2 in FIG. 1 showing various components included in urine collection device shown in FIG. 1.

Referring to FIGS. 1 and 2, an exemplary embodiment of a urine collection device 10 according to the invention includes a chamber assembly 12. The chamber assembly 12 includes a thin layer of wicking material 14 and a porous material 16. The porous material 16 is configured to form a continuous ring-like chamber 18 in which urine can be collected for transport; and the wicking material 14 is disposed about the porous material 16. The chamber 18 has a port 20 for receiving a tube 22 so that urine collected within the chamber 18 can be transported from the chamber 18 by being drawn from the chamber 18 when a partial vacuum is applied within the chamber 18 via the received tube 22. The received tube 22 extends past the port to within the chamber 18. The chamber assembly 12 is dimensioned and configured to define an opening 28 through which the head of a penis can be inserted.

In an alternative embodiment (not shown), the porous material is configured to form a discontinuous C-shaped chamber in which urine can be collected for transport, with opposing portions of the chamber assembly being sufficiently adjacent as to define an opening through which the head of a penis can be inserted.

A flexible sheet of impermeable material 30 is so attached to the chamber assembly 12 as to cover one side of the opening 28 and thereby provide a receptacle 32 for receiving the head of an inserted penis. Urine flowing into the receptacle 32 from the penis can be drawn through the wicking material 14 and the porous material 16 into the chamber 18 when a partial vacuum is applied within the chamber 18 via the tube 22.

In the exemplary embodiment shown in FIG. 2, the sheet of impermeable material 30 is so dimensioned in relation to the breadth of the opening 28 as to extend sufficiently away from the chamber assembly 12 as to provide adequate space in the receptacle to receive the head of the penis.

The layer of impermeable material 30 further covers at least the exterior sides of the chamber assembly 12; and in the exemplary embodiment shown in the Drawing, the layer of impermeable material 30 further covers a portion of the interior sides of the chamber assembly 12.

The layer of impermeable material 30 is so attached to the chamber assembly 12 by an adhesive material as to maintain the chamber assembly 12 in the configuration defining the opening 28, as shown in FIG. 1. In another embodiment (not shown), retainer clips or other fasteners attach the impermeable material to the chamber assembly.

The device 10 further includes a cushion 34, which is disposed in the receptacle 32 within the opening 28 for receiving the head of an inserted penis. The cushion 34 is so disposed over the layer of impermeable material 30 as to contact the wicking material 14 of the chamber assembly 12. The cushion 34 includes a layer of wicking material 36, such as medical gauze, disposed over a bed of porous material 38.

In the exemplary embodiment, the wicking material 14 is medical gauze. In other embodiments other wicking materials are used for the wicking material.

In the exemplary embodiment, the porous material 16 is provided as a web of a spun plastic material, such as nylon or polyester. In other embodiments, other materials are used as the porous material.

In the exemplary embodiment, the chamber 18 is formed by folding together opposite sides of a web of spun plastic material, whereby the chamber 18 does not necessarily have a closed cross-section as shown in FIG. 2.

In FIGS. 1 and 2, the relative dimensions of the various components are not shown to scale.

Different embodiments of a male urine collection device according to the invention are dimensioned and configured for use in both adult and pediatric applications, and for veterinary applications involving animals of different species and sizes.

When a man is lying on his back with the head of his penis disposed within the receptacle 32, urine flowing from the penis runs down the inner sides of the receptacle 32 between the layer of porous material and the sheet of impermeable material 30, through which the urine flows into the chamber 18 and thence to the outlet port 20. The urine collection device 10 can thus advantageously capture urine as it flows against gravity without having to attach a catheter to the penis.

The benefits specifically stated herein do not necessarily apply to every conceivable embodiment of the present invention. Further, such stated benefits of the present invention are only examples and should not be construed as the only benefits of the present invention.

While the above description contains much specificity, these specifics are not to be construed as limitations on the scope of the present invention, but rather as examples of the embodiments described herein. Other variations are possible and the scope of the present invention should be determined not by the embodiments described herein but rather by the claims and their legal equivalents.

The invention claimed is:

1. A device that can be used to collect urine flowing from the penis of a person or an animal in such a manner that the urine can be readily transported from the device as the urine is being collected, the device comprising:
   a chamber assembly in which wicking material is disposed about porous material that is configured to form a chamber in which urine can be collected for transport, with the chamber assembly having a port for receiving a tube so that urine collected within the chamber can be transported from the chamber by being drawn from the chamber when a partial vacuum is applied within the chamber via said received tube, and with the chamber assembly being dimensioned and configured to define an opening through which the head of a penis can be inserted, the chamber including at least one substantially unoccupied gap; and
   a layer of impermeable material attached to the chamber assembly as to cover one side of the opening and thereby provide a receptacle for receiving the head of said inserted penis, from which receptacle urine flowing from said penis can be drawn through the wicking material and the porous material into the chamber when said partial vacuum is applied within the chamber via said tube, wherein the wicking material and the layer of impermeable material define the chamber therebetween.

2. The device according to claim 1, wherein the impermeable material further covers at least the exterior sides of the chamber assembly.

3. The device according to claim 1, wherein the layer of impermeable material is so attached to the chamber assembly as to maintain the chamber assembly in said configuration.

4. The device according to claim 1, further comprising a cushion disposed in the receptacle within the opening for receiving the head of said inserted penis, with the cushion being so disposed over the layer of impermeable material as to contact the wicking material of the chamber assembly.

5. The device according to claim 4, wherein the cushion includes a layer of wicking material disposed over a bed of porous material.

6. The device according to claim 1, wherein said tube is received by the port and extends to within the chamber.

7. The device according to claim 1, wherein the wicking material exhibits a substantially uniform thickness.

8. The device according to claim 1, wherein the porous material exhibits a substantially uniform thickness.

9. The device according to claim 1, wherein the wicking material is spaced from an outlet by the porous material.

10. The device according to claim 1, wherein the wicking material includes a gauze.

11. The device according to claim 1, wherein the porous material includes a spun plastic material.

12. The device according to claim 11, wherein the spun plastic material includes at least one of nylon or polyester.

13. The device according to claim 1, wherein the wicking material includes a first portion and a second portion, a direction that the wicking material extends changes abruptly where the wicking material of the first portion and the second portion meet.

14. The device according to claim 1, wherein the layer of impermeable material is attached to the chamber assembly by an adhesive material.

15. The device according to claim 1, wherein the layer of impermeable material is attached to the chamber assembly by a fastener.

16. The device according to claim 1, wherein the wicking material and the impermeable material covering a portion of the interior sides of the chamber assembly defines a receptacle configured to receive a penis.

17. The device according to claim 1, wherein the impermeable material is disposed on a portion of the at least one interior side of the chamber assembly.

18. A system that can be used to collect urine flowing from the penis of a person or an animal in such a manner that the urine can be readily transported from the device as the urine is being collected, the system comprising:
   a male urine collection device including:
      a chamber assembly in which wicking material is disposed about porous material that is configured to form a chamber in which urine can be collected for transport, with the chamber assembly having a port for receiving a tube so that urine collected within the chamber can be transported from the chamber by being drawn from the chamber when a partial vacuum is applied within the chamber via said received tube, and with the chamber assembly being dimensioned and configured to define an opening through which the head of a penis can be inserted, the chamber including at least one substantially unoccupied gap; and
      a layer of impermeable material attached to the chamber assembly as to cover one side of the opening and thereby provide a receptacle for receiving the head of said inserted penis, from which receptacle urine flowing from said penis can be drawn through the wicking material and the porous material into the chamber when said partial vacuum is applied within the chamber via said tube, wherein the wicking material and the layer of impermeable material define the chamber therebetween; and a vacuum device operably coupled to the tube, the vacuum device configured to provide the partial vacuum within the chamber.

19. A device that can be used to collect urine flowing from the penis of a person or an animal in such a manner that the urine can be readily transported from the device as the urine is being collected, the device comprising:

a chamber assembly in which wicking material is disposed about porous material that is configured to form a chamber in which urine can be collected for transport, with the chamber assembly having a port for receiving a tube so that urine collected within the chamber can be transported from the chamber by being drawn from the chamber when a partial vacuum is applied within the chamber via said received tube, and with the chamber assembly being so dimensioned and configured to define an opening through which the head of a penis can be inserted;

a layer of impermeable material attached to the chamber assembly as to cover one side of the opening and thereby provide a receptacle for receiving the head of said inserted penis, from which receptacle urine flowing from said penis can be drawn through the wicking material and the porous material into the chamber when said partial vacuum is applied within the chamber via said tube; and a cushion disposed in the receptacle within the opening for receiving the head of said inserted penis, with the cushion being so disposed over the layer of impermeable material as to contact the wicking material of the chamber assembly, wherein the cushion is distinct from the chamber assembly.

\* \* \* \* \*